(12) United States Patent
Romero et al.

(10) Patent No.: US 7,556,809 B2
(45) Date of Patent: Jul. 7, 2009

(54) ACTIVE ANTIANGIOGENIC THERAPY

(75) Inventors: Mónica Bequet Romero, Ciudad de La Habana (CU); Boris Ernesto Acevedo Castro, Ciudad de La Habana (CU); Jorge Victor Gavilondo Cowley, Ciudad de La Habana (CU); Luis Enrique Fernández Molina, Ciudad de La Habana (CU); Omar Lopez Ocejo, Ciudad de La Habana (CU); Ricardo de la Caridad Silva Rodriguez, Ciudad de La Habana (CU); Alexis Musachio Lasa, Mariel (CU); Ernesto Galban Rodriguez, Ciudad de La Habana (CU); Dania Marcia Vázquez Blomquist, Ciudad de La Habana (CU)

(73) Assignee: Centro De Ingenieria Genetica Y Biotechnologia, Ciudad de La Habana (CU)

( * ) Notice: Subject to any disclaimer, the term of this patent is extended or adjusted under 35 U.S.C. 154(b) by 146 days.

(21) Appl. No.: 10/511,384

(22) PCT Filed: Apr. 11, 2003

(86) PCT No.: PCT/CU03/00004
§ 371 (c)(1),
(2), (4) Date: Apr. 27, 2005

(87) PCT Pub. No.: WO03/086450
PCT Pub. Date: Oct. 23, 2003

(65) Prior Publication Data
US 2005/0175624 A1    Aug. 11, 2005

(30) Foreign Application Priority Data
Apr. 15, 2002  (CU) .................................... 76/02

(51) Int. Cl.
A61K 39/095  (2006.01)
A61K 39/39   (2006.01)
A61K 38/18   (2006.01)
A61K 38/04   (2006.01)
A61K 39/395  (2006.01)
C07K 4/12    (2006.01)

(52) U.S. Cl. .............. 424/185.1; 424/192.1; 424/193.1; 530/328; 530/399

(58) Field of Classification Search .................. None
See application file for complete search history.

(56) References Cited

U.S. PATENT DOCUMENTS
5,712,380 A * 1/1998 Kendall et al. ............. 536/23.5
6,149,921 A * 11/2000 Rodriguez et al. ......... 424/277.1

FOREIGN PATENT DOCUMENTS
WO    WO 99/45018    * 9/1999
WO    WO 00/53219      9/2000

OTHER PUBLICATIONS

Stryer et al, in Biochemistry, Third edition, W H Freeman Company, New York, pp. 31-33, 1998.*
Ngo et al., The Protein Folding Problem and Tertiary Structure Prediction, pp. 492-495, 1994.*
Leggatt et al, J Immunology 161: 4728-4735, 1998.*
Kobrin et al, J Immunology 146: 2017-2020, 1991.*
Stacker et al, J Biol Chemistry 274(49): 34884-92, Dec. 1999.*
Lu et al, J Biol Chemistry 275(19): 14321-14330, May 2000.*
Siemeister et al, J Biol Chemistry 273(18): 11115-11120, 1998.*
Davidoff, Andrew M., et al., "Bone Marrow-derived Cells Contribute to Tumor Neovasculature and, When Modified to Express an Angiogenesis Inhibitor, Can Restrict Tumor Growth in Mice", *Clinical Cancer Research* 2001, 7:2870-2879.
Prewett, Marie, et al., "Antivascular Endothelial Growth Factor Receptor (Fetal Liver Kinase 1) Monoclonal Antibody Inhibits Tumor Angiogenesis and Growth of Several Mouse and Human Tumors", *Cancer Research* 1999, 59:5209-5218.
Wei, Yu-quan, et al., "Immunogene therapy of tumors with vaccine based on Xenopus homologous vascular endothelial growth factor as a model antigen", *PNAS* 2001, 98(20):11545-11550.

* cited by examiner

*Primary Examiner*—Phuong Huynh
(74) *Attorney, Agent, or Firm*—Hoffmann & Baron, LLP

(57) ABSTRACT

Application of oligonucleotide and polypeptide sequences of molecules of the family of the vascular permeability factor (VPF), their receptors, and co-receptors, as well as their modifications, in the active immunotherapy of pathologic entities in which course is associated to the increase of angiogenesis.

These procedures can be employed in the single or combined therapy for the treatment of cancer and its metastasis, acute and chronic inflammatory processes, infectious diseases, autoimmune diseases, diabetic and newborn retinopathies, organ transplant rejection, macular degeneration, neovascular glaucoma, hemangioma, and angiofibroma, among others.

2 Claims, No Drawings

ACTIVE ANTIANGIOGENIC THERAPY

This application is a U.S. National Phase Application of International Application No. PCT/CU03/00004 filed on Apr. 11, 2003. The specification of International Application No. PCT/CU03/00004 is hereby incorporated by reference in its entirety.

This application asserts priority to Cuban Application No. CU2002/0076 filed on Apr. 15, 2002. The specification of Cuban Application No. CU2002/0076 is hereby incorporated by reference in its entirety.

BACKGROUND OF THE INVENTION

The present invention is related with the field of biotechnology and pharmaceutical industry, in particular with active immunization employing as targets molecules related with angiogenesis.

The process of formation of new blood vessels from pre-existent ones is called angiogenesis. This event is widely regulated through the equilibrium of pro- and anti-angiogenic factors. Among the diseases in which the course has been related with the induction of pro-angiogenic factors and the formation of new blood vessels in anomalous form are: (a) cancer (both primary tumors and their metastases), (b) acute and chronic inflammatory processes such as asthma, respiratory distress, endometriosis, atherosclerosis, and tissular edema, (c) diseases of infectious origin as the Hepatitis, and Kaposi sarcoma, (d) autoimmune diseases as diabetes, psoriasis, rheumatoid arthritis, thyroiditis, and (e) other diseases and states as the diabetic and newborn retinopathies, organ transplant rejection, macular degeneration, neovascular glaucoma, hemangioma, and angiofibroma (Carmelliet P. y Jain R K. Nature 407:249, 2000; Kuwano M, et al. Intern Med 40:565, 2001). A potentially attractive therapeutic procedure for many of these cases could be based on the inhibition of the activity of the pro-angiogenic factors, that stimulate the anomalous formation of blood vessels, via their neutralization, or that of their receptors, or by eliminating the sources that produces them.

Vascular endothelium growth factors are a family of molecules that induce the formation of new vessels specifically and directly (Leung Science 246:1306, 1989; Klagsburn M, Annual Rev Physiol 33:217, 1991). This family includes the vascular permeability factor, also known as vascular endothelium growth factor VPFNEGF (now denominated VEGF-A), the placenta growth factor PIGF, the platelet derived growth factors PDGF-A and PDGF-B, and other four new molecules structurally and functionally related to VEGF-A designated VEGF-BNRF, VEGF-CNRP, VEGD-D/FIGF, and VEGF-E. (Olofsson B et al. PNAS USA 13:2576, 1996; Joukov V et al. EMBO J. 15:290, 1996; Yamada Y et al. Genomics 42:483, 1997; Ogawa S et al. J Biol Chem 273: 31273, 1998).

VEGF-A is a homodimeric glycoprotein formed by two 23-kDa subunits (Ferrara N, et al. Biochem Biophys Res Comun 165:198, 1989), of which five monomeric isoforms exist, derived from the differential splicing of the same RNA. These include two isoforms that remain attached to the cellular membrane (VEGF 189 and VEGF 206), and three of soluble nature (VEGF 121, VEGF 145, and VEGF 165). VEGF 165 is the most abundant isoform in mammal tissues, except for lung and heart, where VEGF 189 predominates (Neufeld G et al. Canc Met Rev 15:153, 1995), and in placenta, where VEGF 121 expression prevails (Shibuya M A et al. Adv Canc Res 67:281, 1995).

VEGF-A is the most studied and characterized protein of this family, and its alteration has been described in a larger number of diseases. Its over-expression is associated to tumors of different origin and localization, and their metastasis (Grunstein J et al. Cancer Res 59:1592, 1999), chronic inflammatory processes as ulcerative colitis and Crohn's disease (Kanazawa S, et al. Am J Gastroenterol 96:822, 2001), psoriasis (Detmar M, et al. J Exp Med 180:1141, 1994), respiratory distress (Thickeft D R et al. Am J Respir Crit Care Med 164:1601, 2001), atherosclerosis (Celletti F L et al. Nat Med 7:425, 2001; Couffinhal T et al. Am J Pathol 150:1653, 1997), endometriosis (McLaren J. Hum Reprod Update 6:45, 200), asthma (Hoshino M, et al. J Allergy Clin Immunol 107:295, 2001), rheumatoid arthritis and osteoarthritis (Pufe T et al. J Rheumatol 28:1482, 2001), thyroiditis (Nagura S et al. Hum Pathol 32:10, 2001), diabetic and newborn retinopathies (Murata T et al. Lab Invest 74:819, 1996; Reynolds J D. Paediatr Drugs 3:263, 2001), macular degeneration and glaucoma (Wells J A et al. Br J Ophthalmol 80:363, 1996; Tripathi R C et al. Ophthalmology 105:232, 1998), tissular edema (Kaner R J et al Am J Respir Cell Mol. Biol. 22:640 2000; Ferrara N Endocrinol Rev 13:18, 1992), obesity (Tonello C et al. FEBS Left 442:167, 1999), hemangiomas (Wizigmann S y Plate K H Histol Histopathol 11:1049, 1996), in the synovial fluid of patients with inflammatory arthropathies (Bottomley M J et al Clin Exp Immunol 119:182, 2000), and associated to transplant rejection (Vasir B, et al. Transplantation 71:924, 2001). In the particular case of tumors, the cells expressing the three basic isoforms of VEGF-A: 121, 165, and 189, are the ones that grow faster in vivo; while in final stages most tumors limit expression to the VEGF 165 isoform, or, in its absence, to a combination of 121 and 189 that far from being additive, evidences a cooperation that strengthens the tumor vascular network (Grunstein J. Mol. Cell Biol 20:7282, 2000).

PIGF, described in 1991, is not able to induce endothelial proliferation in its homodimeric form (Maglione D et al. Proc Natl Acad Sci USA 88:9267, 1991, DiSalvo J et al. J Biol Chem 270:7717, 1995). With PIGF up-regulation, and with it, of the signal transduced via VEGFR-1, the endothelial cells amplify their responses to VEGF during the change to the angiogenic phenotype associated to certain pathologies (Carmeliet P et al. Nat Med 7:575, 2001). PIGF expression has been related to the vascularization of human meningioma and glioma (Nomura M et al. J Neurooncol 40:123, 1998). This molecule forms heterodimers with VEGF 165, with pro-angiogenic activity, and their over-expression has been described in the conditioned media of some tumor cell lines (Cao Y et al. J Biol Chem 271:3154,1996), and associated to the evolution of rheumatoid arthritis and to primary inflammatory arthropathies, in general (Bottomley M J et al. Clin Exp Immunol 119:182, 2000).

The over-expression of the rest of the members of the VEGF family, less studied, is also associated to a number of pathologies. VEGF-B has been related to breast, ovary, and kidney tumors, and to melanomas and fibrosarcomas (Sowter H M, et al. Lab. Invest. 77:607, 1997; Salven P Am. J. Pathol. 153:103, 1998, Gunningham S P et al. Cancer Res 61:3206, 2001). The differential expression of the VEGF-B 167 isoform in vitro has been reported in tumor cells of diverse origin (Li X, et al. Growth Factors 19:49, 2001). VEGF-C and VEGF-D are involved in the regulation of lymphatic vessels formation (Joukov V. et al EMBO J. 15: 290, 1996), and VEGF-C over-expression is associated to tissular edemas, to tumors of the breast, lung, head and neck, esophagus, and stomach, lymphomas, prostate cancer, and metastatic nodes (Kajita T, et al. Br J Cancer 85:255, 2001; Kitadi Y, et al Int J Cancer 93:662, 2001; Hashimoto I, et al. Br J Cancer 85:93, 2001; Kinoshita J, et al. Breast Cancer Res Treat 66:159, 2001; Ueda M, et al. Gynecol Oncol 82:162, 2001; Salven P Am. J. Pathol. 153:103, 1998; O-Charoenrat P et al. Cancer 92:556, 2001). In the case of VEGF-D, its over-expression by tumor cells is related to an in vivo increase of lymphatic vasculature in the tumors and the increase of metastasis in lymphatic nodes (Stacker S A, et al. Nat Med 7:186, 2001; Marconcini L et al. Proc Natl Acad Sci USA 96:9671, 1999).

The alterations on endothelial cell function induced by the molecules of the VEGF family are mediated by their binding to cell receptors of the type tyrosine kinase class 3, that so far include: VEGFR1 (Flt1), VEGFR2 (KDR/Flk1), and VEGFR3 (Flt4) (Kaipainen A J. Exp. Med. 178:2077, 1993). The N-terminal domain 2 has been identified as responsible of the binding to the ligands, favoring the phosphorilation of the cytoplasmatic domain and transduction of the signal (Davis-Smyth T et al EMBO 15:4919, 1996).

Ligands identified for VEGFR1 include VEGF-A, PIGF, and VEGF-B, in decreasing order of affinity (Shibuya M Int J Biochem Cell Biol 33: 409, 2001). In endothelial cells, this receptor captures the circulating VEGF (Gille H et al *EMBO J.* 19:4064, 2000). The binding of VEGF-A to the VEGFR1 expressed in cells of the hematopoyetic lineage affects significantly the activation of transcriptional factor NFκB in the precursors of dendritic cells, and in B and T lymphocytes. This last interaction is relevant in the in vivo establishment of an unfavorable immunologic balance, where dendritc cells maturation and the fraction of T lymphocytes are reduced, a phenomenon observed on immunosupressed patients and in particular, with cancer (Dikov M M et al Canc Res 61:2015, 2001; Gabrilovich D et al. Blood 92:4150, 1998). Over-expression of VEGFR1 has been related with psoriasis, endometrial cancer and hepatocellular carcinoma (Detmar M, et al. J Exp Med 180:1141, 1994; Ng IO Am J Clin Patol 116:838, 2001; Yokoyama Y et al Gynecol Oncol 77:413, 2000).

The VEGFR2 receptor (KDR/Flk1) mediates the biological effects of VEGF-A, and also binds VEGF-C and VEGF-D. This receptor is expressed differentially on activated endothelium and in some cell lines of tumor origin where it establishes autocrine pathways with the secreted VEGF. Apart from being involved in the already mentioned pathologies that are related with the over-expression of its ligands, the over-expression of VEGFR2 has been related with the progression of endometrial cancer (Giatromanolaki A et al, Cancer 92:2569, 2001), malignant mesothelioma (Strizzi L et al. J Pathol 193:468, 2001), astrocytic neoplasms (Carroll R S et al. Cancer 86:1335, 1999), primary breast cancer (Kranz A et al. Int J Cancer 84:293, 1999), intestinal type gastric cancer (Takahashi Y et al Clin Cancer Res 2:1679, 1996), multiform glioblastoma, anaplastic oligodendroglioma, and necrotic ependimoma (Chan A S et al. Am J Surg Pathol 22:816, 1998). Over-expression of KDR has also been associated to the autosomic disease VHL and to hemangioblastoma (Wizigmann-Voos S et al Cancer Res 55:1358, 1995), to the progression of diabetic retinopathy (Ishibashi T. Jpn J Ophthalmol 44:323. 2000) and, in combination with Flt-1 over-expression, to the delayed-type hypersensitivity reactions (Brown L F et al J Immunol 154:2801,1995).

Lymphangiogenesis mediated by VEGF-C and VEGF-D results from their binding to the FLT4 receptor or VEGFR3, expressed in the lymphatic endothelium. In some cases, even when over-expression of the ligands is not present, the over-expression of the receptor has been related to an adverse prognosis in the course of a group of pathologic entities, including: diabetic retinopathy (Smith G. Br J Ophthalmol 1999 April;83(4): 486-94), chronic inflammation and ulcers (Paavonen K et al, Am J Pathol 156:1499, 2000), the establishment of metastasis in lymphatic nodes and progression of breast cancer (Gunningham S P. Clin Cancer Res 6:4278, 2000 Valtola R et al. Am J Pathol 154:1381, 1999), associated to nasopharyngeal tumors and squamous oral carcinomas (Saaristo A et al. Am J Pathol 157:7, 2000; Moriyama M et al. Oral Oncol 33:369, 1997). Moreover, the over-expression of VEGFR3 is a sensitive marker of Kaposi sarcoma, type Dabska hemangioendothelioma and of cutaneous tymphangiomatosis (Folpe A L et al. Mod Pathol 13:180, 2000; Lymboussaki A et al. Am J Pathol 153:395, 1998).

Recently, two receptors were identified for VEGF named NRP1 and NRP2. These belong to the neurophilins family (NRP), and act as co-receptors for some specific isoforms of proteins of the VEGF family: VEGF-$A_{145}$, VEGF-$A_{165}$, VEGF-$B_{167}$ and PIGF1, increasing their mitogenic capacity. The expression of NRP1 has become a marker of the aggressiveness of prostate cancer, has been related to the increase of angiogenesis in melanomas, and with apoptosis escape events in breast cancer (Latil A et al. Int J Cancer 89:167, 2000; Lacal P M J Invest Dermatol 115:1000, 2000; Bachelder R E Cancer Res 61:5736, 2001). The coordinate over-expression of NRP1, KDR, and VEGF-$A_{165}$ have been related to the fibrovascular proliferation in diabetic retinopathy cases and rheumatoid arthritis (Ishida S. et al. Invest Ophthalmol Vis Sci 41: 1649, 2000; Ikeda M. Et al. J Pathol 191:426, 2000). NRP2 is over-expressed in osteosarcomas where it promotes angiogenesis and tumor growth (Handa A et al. Int J Oncol 17:291, 2000).

Most of the therapeutic strategies based on angiogenesis inhibition, especially in cancer treatment, are based in the blockade of molecules of the VEGF family and their receptors, with clinical trials in course using: (1) monoclonal antibodies blocking VEGF or the KDR receptor, (2) metalloproteinase inhibitors, as Neovastat and Prinomastat, (3) VEGF inhibitors as Thalidomide, Suramin, Troponin I, and IFN-α and Neovastat, (4) blockers of VEGF receptors as SU5416, FTK787 and SU6668, (5) inducers of tumor endothelium apoptosis, as Endostatin and CA4-P, and (6) ribozymes that decrease VEGF or VEGF receptors expression (Angiozyme). Due to the high homology between human VEGF and its receptors KDR and Flt-1 with their murine homologs (~90%, 81%, and 89%, respectively), many animal models are used routinely to evaluate the preclinical effectiveness of antiangiogenic compounds directed to this system (Hicklin D J et al. DDT 6:517, 2001).

Passive administration of antibodies to VEGF or VEGFRs is successfully tested in different clinical phases in humans (Hicklin D J et al. DDT 6:517, 2001). The anti-VEGF humanized monoclonal antibody A.4.6.1 (Genentech, San Francisco, United States) is in phase III clinical trial for the treatment of colon, breast, kidney, and lung tumors (Kim, K J et al. Nature 362:841, 1993; Boersig C. R&D Directions October 7:44, 2001). In particular, for the case of the KDR receptor, a monoclonal antibody has been developed (IMC-1C11, ImClone) that recognizes the N-terminal extracellular domain of this receptor, and inhibits proliferation and migration of leukemic human cells, increasing survival of xenotransplanted mice. At present, its effect is being studied in patients with colon cancer metastasis (Dias S et al. J Clin Invest 106:511, 2000). In the aforementioned trials, the absence of concomitant adverse effects with the application of these monoclonal antibodies has been demonstrated.

Notwithstanding the previous, a therapeutic modality not yet employed for the blockade of neoangionegesis is specific active immunotherapy (SAI). In the SAI of cancer, antigens as peptides, proteins or DNA are employed, mixed with appropriate adjuvants. SAI procedures pursue the stimulation of an immune response, both of the humoral (activation of B-lymphocytes), and cellular types (activation of T helper, and cytotoxic lymphocytes, and natural killer cells), associated to dendritic cell function as professional presenting cells in the MCHI and MHC II contexts (Bystryn J C, Medscape Hematology-Oncology 4:1, 2001; Parker, K C et al., J. Immunol 152:163, 1994; Nestle F O et al., Nature Medicine 7:761, 2001; Timmerman J M, Annual Review Medicine 50:507, 1999).

SAI is a rapidly growing field of experimental and clinical research, with attractive applications, especially in oncology, where more than 60 undergoing clinical trials based in procedures of SAI are reported, which surpass at present the clinical trials based on the use of monoclonal antibodies. In the particular case of cancer, the antigens used as immunogens for SAI are selected because of their physiological relevance and difficulty of being substituted in the processes of tumor phenotypic drift (Bodey B et al., Anticancer Research 20: 2665, 2000), and because of their high specific association with the growth and evolution of tumor tissues.

The strategy of treating cancer using SAI also considers preferably the identification of antigens expressed in different tumor types, what could increase the number of indications for the same vaccine preparation. Examples of these are carcinoembryonic antigen (CEA), HER2-neu, human telomerase, and gangliosides (Greener M., Mol Med Today 6:257 2000; Rice J, et al. J Immunol 167:1558, 2001; Carr A et al, Melanoma Res 11:219, 2001; Murray J L, et al. Semin Oncol 27:71, 2000).

In human tumors, VEGF is over-expressed in the tumor compartment (Ferrara, N. Curr. Top. Microbiol. Immunol. 237:1, 1999), and high levels of VEGF and its receptors have been demonstrated in the tumor-associated vasculature (Brekken R A. J Control Release 74:173, 2001). The stromal cells also produce VEGF in response to the stimulus of transformed cells, with the result that when tumor cells are removed, VEGF levels persist in the patients. The presence of VEGF and its receptors have a practical value for the establishment of prognosis and staging in cases of prostate, cervix, and breast tumors (George D J et al. Clin Cancer Res 7:1932, 2001; Dobbs S P et al. Br J Cancer 76:1410, 1997; Callagy G et al. Appl Immunohistochem Mol Morphol 8:104, 2000). On the other hand, VEGF is also within the group of soluble factors that, together with other cytokines like IL-10, TNF-α and TGF-β, (Ohm J E & Carbone D P, Immunol Res 23:263, 2001), could be implicated in the immunosuppression that characterizes cancer patients (Staveley K, et al. Proc Natl Acad Sci USA 95:1178, 1998; Lee K H, et al. J Immunol 161:4183, 1998). This immunosuppressive effect seems to be related to its binding to the FIt1 receptor (Gabrilovich D et al. Blood 92:4150, 1998).

The present invention describes procedures of SAI in experimental tumors using molecules of the VEGF family and their receptors. The antitumoral effects obtained could be based in at least four different mechanisms, without discarding their possible combinations: (a) direct destruction of cancer and stromal cells producing VEGF, by cytotoxic lymphocytes, (b) damaging of endothelial cells of tumor-associated vessels due to the capture or neutralization of the circulating VEGF via antibodies, (c) direct destruction of endothelial cells that express VEGF receptors, by cytotoxic lymphocytes or complement fixing antibodies, (d) activation of a local immune response as a consequence of the capture or neutralization of circulating VEGF, and its consequent elimination of its immunosuppressive effects.

Ideally, these treatments could be used to diminish or avoid the appearance of metastasis, to reduce or eliminate primary tumors as a first or second line therapy, in combination or not with other anti-tumor agents.

Active immunization directed to VEGF family and their receptors could also be efficient in the single or combined therapy of acute and chronic inflammatory processes (asthma, respiratory distress, endometriosis, atherosclerosis, tissular edema), infectious diseases (Hepatitis, Kaposi sarcoma), autoimmune diseases (diabetes, psoriasis, rheumatoid arthritis, thyroiditis, synovitis), diabetic and newborn retinopathies, organ transplant rejection, macular degeneration, neovascular glaucoma, hemangioma, and angiofibroma, among others.

DETAIL DESCRIPTION OF THE INVENTION

According to the present invention, the in vivo administration of oligonucleotide sequences encoding for proteins of the VEGF family, their receptors, co-receptors or their fragments, as well as of their polypeptidic variants, induces a cellular and humoral immune response with antiangiogenic and antitumoral effect.

Immunogens of polypeptidic nature of interest for the present invention, as well as their fragments, can be isolated from their natural sources or obtained by synthesis or recombinant DNA technology. These polypeptides can also be produced fused to proteins having known adjuvant activity, such as p64,K (R. Silva et al U.S. Pat. No. 5,286,484 and EP 0474313), or covalently bound to adjuvants following the polypeptide synthesis. Other available strategies in these cases are the obtainment of the natural polypeptide, its mutated or modified variants, and their fragments, as a part of loops exposed or not in bacterial proteins like OMP1, which are part of immunostimulatory preparations, in this particular case VSSP (R. Perez et al U.S. Pat. No. 5,788,985 and U.S. Pat. No. 6,149,921). Furthermore, it is possible to obtain the polypeptidic immunogen exposed in the surface of a viral particle (HbsAg, VP2 of parvovirus, etc.), bound to specific peptides that target cells or organs specialized in the induction of the immune response (CTLA4, Fc segment of the Ig, etc.), or to proteins capable of increasing biodistribution like VP22.

The principal natural sources of the proteins of interest for the present invention are predominantly expressed in placenta, activated endothelial cells, and tumor cells. The mRNA of these cells or tissues is used to obtain complementary DNA (cDNA) by known methods. The extracted RNA is used as template for the amplification through the polymerase chain reaction (PCR) of the cDNA corresponding to the selected antigen. In each case, primers used are designed according to the characteristics of the vector where the cDNA is going to be inserted and to the previously reported sequences of the protein of interest. Alternatively, and preferably in the case of the receptors amplified by PCR, that are the largest size antigens that are used in the present invention, the coding regions are amplified in two or more overlapping fragments. These fragments include a common ligation site used to assemble the intact DNA, starting with its fragments.

An alternative for the cloning of the antigens of interest is the selection from commercially available DNA libraries derived from human endothelium, or from tumors of this same origin. In some cases, it might be desirable to mutate some of the antigens object of the present invention, in order to avoid, especially with the VEGF family, an angiogenesis induction event produced by vaccination. These mutations are made preferably in the receptor binding sites already described in the literature. For this, primers are designed that cover both ends of the desired molecule, and the PCR products are used as template to obtain the mutated molecule. These mutated variants lack biological activity but reproduce the immunogenic properties of the selected antigen.

The cDNA molecules obtained by the methods described earlier are administered in a proper vector, being this a virus, a plasmid, a bacterial artificial chromosome, or similar. The vector carries the elements needed for the adequate expression of the gene in target cells, as well as the rest of elements that allows it to be produced in the host cellular system according to its nature. DNA molecules of the present invention might contain one or more genes of interest, constituted by one or more nucleic acids (cDNA, gDNA, synthetic or semi-synthetic DNA, or similar) that when transcribed or translated (when appropriate) in target cells generates the products with therapeutic/vaccine value.

Generally, the gene of the vaccine therapeutic product according to the invention is under the control of a transcriptional promoter that is functional in the target cell or the organism (mammals), as well as of a 3' end region that contains the signals needed for termination and polyadenilation of the mRNA of the product of interest, allowing its expression. The promoter can be the natural promoter of the gene or a heterologous promoter transcriptionally active in the target cell. The promoter can be from eukaryotic or viral origin. Among eukaryotic promoters, it is possible to use any promoter or derived sequence that stimulates or represses the gene transcription, specifically or not, inducible or not, in a strong or weak manner. Additionally, the promoter region can be modified by the insertion of activators or inductor sequences, allowing the tissue-specific or predominant expression of the gene in question.

Besides, the gene of interest can contain a signal sequence for subcellular localization, in a way that its cellular localization or secretion could be modified in the cell where it is expressed, or elsewhere, once synthesized. It can also contain a sequence encoding for a region of specific binding to a ligand specific of immune tissue, being directed to the site where the response is generated, with the obtainment of the therapeutic/vaccine effect.

Additionally, the gene of interest can be preceded by the coding sequence for the mRNA replication machinery, in a way that mRNA is amplified in the target cell, increasing the expression of said gene, and with it, the therapeutic/vaccine effect according to the invention. The replication machinery in question could be of alphavirus origin (Schlesinger S., Expert Opin Biol Ther. 1:177, 2001), more specifically derived from the Sindbis or Semliki viruses, or similar. In this particular case, the gene of interest is under the transcriptional control of a subgenomic promoter that allows the amplification of its mRNA in target cells, once the molecules according to the present invention have been internalized. Furthermore, the DNA vector might contain sequences that permit the replication of the molecules, which are objects of the present invention in mammalian cells. This allows an increase in the expression levels and/or of the therapeutic/vaccine effect (Collings A., Vaccine 18: 4601, 1999).

The DNA vector can be purified using standard techniques for plasmid DNA purification. These techniques include the method of purification by cesium chloride density gradient, in the presence of ethidium bromide, or alternatively, the use of ionic exchange columns or any other exchanger or method to separate DNA molecules (Ferreira G N, et al, Trends Biotechnol. 18:380, 2000).

The present invention includes the use of plasmidic DNA vectors, preferably those of the PAEC family of compact vectors for DNA immunization and gene therapy in humans (Herrera et al, Biochem. Biophys. Res. Commu. 279: 548, 2000). This family comprises vectors pAEC-K6 (Access number AJ278712), pAEC-M7 (Access number AJ278713), pAEC-AΔ2 (Access number AJ278714), pAEC-SPE (Access number AJ278715) and pAEC-SPT (Access number AJ278716). These vectors contain only the essential elements for the expression of the product of interest in mammalian cells, including human cells, and a replication unit in *Escherichia coli*. The transcriptional unit is formed by the immediate early promoter of human cytomegalovirus (CMV), a versatile multicloning site for the insertion of the product of interest, and the sequences for transcriptional termination and polyadenilation derived from simian virus 40 (SV40). In the replication unit, the vector contains the gene for kanamycin resistance (Tn903), and a pUC19 replication origin (ColE1), in order to guarantee a high copy number and the selection of the bacteria that bear the plasmid of interest.

Furthermore, the present invention includes the use of plasmidic DNA vectors, preferably those of the PMAE family of compact vectors for DNA immunization in humans. These contain the same functional elements in bacteria as PAEC series, as well as the CMV immediate early promoter and the multicloning site. Additionally, they bear a synthetic intron and a synthetic sequence for transcription termination and polyadenilation, derived from rabbit β-globin. It has been reported that with sequences similar to the latter it is possible to obtain higher expression levels of the cloned gene (Norman J A et al, Vaccine 15: 801, 1997). Moreover, the vectors of this series include consecutive repetitions of immunostimulatory sequences (CpG motives), that stimulate innate immune system in both mice and humans, with the consequent activation of a humoral and cellular response against the molecule of interest (Krieg A M, Vaccine 19:618, 2001).

The immunization with recombinant virus (adenovirus, adeno-associated, vaccinia, chickenpox virus, canarypox virus, among others) produces a potent cytotoxic cellular response in the hosts. To introduce the sequence of interest in the recombinant virus vectors that have integration sequences and promoters that are particular for each virus type, are used. This strategy is also included in the scope of the present invention, and chickenpox virus and the pFP67xgpt vector are preferably used. The pFP67xgpt vector is used to clone genes under a strong early/late promoter of synthetic nature between the open reading frames 6 and 7 of a fragment of 11.2 kB BamHI of the chickenpox virus FP9. This plasmid also contains the Ecogpt controlled by the vaccinia promoter p7.5K, which is used to identify recombinant virus.

Other alternative of the present invention consists of the immunization with proteins of the VEGF family and their receptors and/or co-receptors. cDNA molecules obtained as previously described are cloned in vectors for expression in virus, yeast, phage, plants, or superior cells, in order to obtain the protein variants of the antigens, after their sequence has been verified by the traditional methods of automatic sequencing. Several vectors for expression have been described and used for the obtainment of recombinant proteins. These vectors contain, at least, a sequence that controls the expression operatively linked to the sequence of the DNA or fragment to be expressed. Examples of sequences useful for the control of expression are: the systems lac, trp, tac, and trc, the promoter regions and the principal operator of lambda phage, the controller region of the surface protein fd, the glycolytic promoters of yeast (for example, the 3-phosphoglicerate kinase), the promoters of yeast acid phosphatase (for example, Pho5), the yeast promoters for the mating alpha factor, and the promoters derived from polyoma, adenovirus, retrovirus, simian virus (for example, the early/late promoters of SV40), and other known sequences that regulate the expression of genes in prokaryotic and eukaryotic cells, their viruses, and their combinations.

The hosts used for the replication of these vectors and the obtainment of the recombinant proteins object of the present invention include prokaryotic and eukaryotic cells. The prokaryotic comprise *E. coli* (DHI, MRCI, HB101, W3110, SG-936, X1776, X2282, DH5a), *Pseudomonas, Bacillus subtilis, Streptomices*, and others. The eukaryotic include yeast and fungi, insects, animal cells (for example, COS-7 and CHO), human, and plant cells, and tissue cultures, among others. After the expression in the system of choice in an adequate media, the polypeptides or peptides can be isolated by known procedures.

Use of Adjuvants

Even when vaccination with naked DNA or proteins has shown to be effective in certain animal models, the patients affected by tumors or autoimmune diseases present a challenge to the therapeutic strategy proposed by the present invention. To favor the immune response, the DNA or protein vaccines can be combined with immunopotentiators already described like: mineral salts (ex., Aluminum hydroxide, aluminum phosphate, calcium phosphate); immunoestimulators like: cytokines (ex., IL-2, IL-12, GM-CSF, IFN-α, IFN-γ, IL-18), molecules (ex., CD40, CD154, invariant chain of MHC type 1, LFA3); saponins (ex., QS21), MDP derivatives, CpG oligos, LPS, MPL and polyphosphazenes; lipidic particles like: emulsions (ex., Freund, SAF, MF59), liposomes, virosomes, iscoms, co-chelators; microparticular adjuvants like PLG microparticles, poloxamers, of viral type (ex., HBcAg, HCcAg, HBsAg), and of bacterial type (ie., VSSP, OPC); and mucosal adjuvants like heat-labile enterotoxin (LT), cholera toxin, and mutant toxins (ex., LTK63 y LTR72), microparticles and polymerized liposomes. In the case of DNA vaccination, the expression of the antigen of interest could be combined with some of the immunopotentiator molecules already mentioned, on a bi-cistronic vector.

The experimental situations detailed in the examples demonstrate that DNA can be coupled in a non-covalent manner to some of the mentioned particles and that the use of these mixtures reduce the optimal concentration to obtain an anti-tumor response, similar to those described for higher doses of naked DNA.

Administration to a Mammal

For the therapeutic applications, the vaccine preparations of the present invention are administered to a mammal, preferably a human, in a dose pharmaceutically acceptable, by the following routes: mucosal, subcutaneous, intramuscular, peritoneal, intra-lymphatic, topic, and by inhalation, among others. These could be administered on the tissue interstitial space, including: muscle, skin, brain, lung, liver, bone marrow, spleen, thymus, heart, lymph nodes, blood, bone, cartilage, pancreas, kidney, bladder, stomach, intestine, testicles, ovary, uterus, rectum, eye, glands, and connective tissue. In the case of vectors for oligonucleotide transfer, their expression is preferably directed to somatic differentiated cells, though they may be directed to non-differentiated or less differentiated cells like skin fibroblasts and blood pluripotent cells.

The doses of the immunogen could be administered in pharmaceutically accepted vehicles without toxicity or therapeutic effects. Examples of these vehicles include: ionic exchangers, alumina, aluminum esthearates, lecitine, seric proteins like albumin, buffer solutions, like phosphates, glycine, sorbic acid, potassium sorbate, partial glyceride mixtures of saturated fatty acids of plant origin, water, salts, or electrolites, like protamine sulphate, di-sodic hydrogen phosphate, sodium chloride, zinc salts, colloidal silica, magnesium trisilicate, polivynil pirrolidone, substances base on cellulose and polyethylene glycol. In the present invention, preferably phosphate buffers as vehicles of the vaccine preparations are used.

In the case of the use of proteins and peptides, these can be conjugated in covalent or non-covalent manner to molecules known as carriers that act like adjuvants. Among these molecules are: KLH, p64K, OPC (Musacchio A et al, Vaccine 19; 3692, 2001), and VSSP. The combination of naked DNA, viral vectors, and protein immunogens is an alternative also included within the scope of the present invention. In an advantageous manner, plasmid DNA administration allows the generation of formulations with one or more molecules of interest in the vaccine preparation. Thus, molecules according to the present invention can be administered in vaccine schedules through the combination of different types of vectors (variant of induction re-stimulation, with DNA, proteins, viral vectors).

DNA vectors could be directly administered to the patient, or host cells can be in vivo or ex vivo modified with these vectors. This last strategy can be combined with the insertion by site-specific recombination or the immunization by somatic transgenesis that directs the vector expression to specific cells. Furthermore, bacterial hosts of DNA vectors could be used as their vehicles of transfer in vivo.

In this way, the molecules carrying the genes according to the present invention could be used in the form of naked DNA, or in combination with different vectors: chemical/biochemical/biologic, natural/synthetic or recombinant. These molecules can be coupled or combined with cationic peptides, compacting molecules (ex. PEG, PEI), nuclear localization peptides (NLP), etc. These could be administered also together with cations capable of forming DNA precipitates, as a part of liposomal preparations to which the molecules have been added previously to the membrane fusion, and in synthetic vectors of lipid nature, or formed by cationic polymers (ex. DOGS or DOTMA). For the administration of the DNA vectors, chimeric proteins able to compact DNA and mediate the transport of the complex formed, and its selective endocytosis by specific cells, can also be used. DNA molecules carrying the therapeutic/vaccine genes according to the invention could be used for the genetic transfer to cells using physical methods of transfer, like particles bombardment, electroporation (in vitro, in vivo or ex vivo), or directly in vivo by topic application, inhalation by particulation, etc. The live vectors include adenoviral particles or the same hosts where the molecules according to the present invention have been generated.

The doses of polypeptides and/or oligonucleotides to be used can be established according to different parameters, in particular depending on the gene or protein administered as an immunogen, the route of administration, the pathology to be treated, the period of treatment, and in the case of using oligonucleotides, of the vector used for immunization. A change in dose schedule or administration route different to those described in the following examples, do not separate from the principle or precept of the present invention, being possible to achieve an optimization of the immunization schemes to obtain a better response.

Therapeutic Uses

The present invention has advantages over passive immunotherapy, which is in advanced phases of clinical trials using the same molecules as targets. In comparison with passive transfer of immunity through the administration of monoclonal antibodies (ex. Anti-VEGF), the immunization, be it with the protein or the oligonucleotide, has the advantage of inducing the endogenous production of antibodies and in addition the proliferation and expansion of specific cytotoxic CD8+ lymphocytes.

The present invention has advantages over the therapeutic strategies directed to block VEGF-VEGFRs system, mainly because these strategies only diminish the levels of circulating VEGF or block KDR. The strategy proposed, apart from achieving the mentioned effects, also destroys the source of VEGF (that is, the tumor cells and associated stroma) and/or the cells expressing their receptors (tumor endothelium and some tumor cells). Previous work done in this area only describe a humoral response as a principal component of the observed effect. Without the intention of limiting the scope of the present invention to a particular mechanism, the examples show that, besides from the humoral specific response, the vaccine compositions are able to elicit a CD8+ cellular response that cooperates with the humoral response; and that in the tumor context, the combination of both are relevant to obtain an anti-tumor effect, the previous observed in example 9.

It is possible that the cytotoxic cellular response is mediated by the recognition of some of the peptides that appear in Tables 1 and 2. In these, some peptidic segments appear, that could be relevant in the cellular response directed to selected targets in VEGF family, its receptors and co-receptors. This information was obtained through computer analyses on public databases from NIH and Heidelberg Institute using BIMAS and SYFPHEITI software, respectively. The peptides marked and other sequences derived from the antigens of interest could be used for the active immunotherapy of the already described pathologies, as a single or combined treatment, and as part or not of molecules with adjuvant capacities. These peptides can also be used in their oligonucleotide variants with vaccine purposes.

The methods to inhibit angiogenesis and the pathologic conditions associated to this event, comprise the administration of an effective amount of the DNA or protein of some of the molecules described in this invention, by any of the routes, and with the use of some of the previously described immunopotentiators or adjuvants, to a mammal. This mammal is preferably a human.

A non-reversible and unregulated increase of angiogenesis has been related to a wide group of diseases. The system that comprises the VEGF family, its receptors and co-receptors is over-expressed in many of these pathological conditions, as it has been described before. In this way, the therapeutic strategies proposed by the present invention result effective in the treatment of: (a) cancer (both primary tumors and their metastasis), (b) acute and chronic inflammatory processes like asthma, respiratory distress, endometriosis, atherosclerosis, and tissular edema, (c) diseases of infectious origin like Hepatitis and Kaposi sarcoma, (d) autoimmune diseases like diabetes, psoriasis, rheumatoid arthritis, thyroiditis, and (e) other diseases and states such as diabetic and newborn retinopathies, organ transplant rejection, macular degeneration, neovascular glaucoma, hemangioma and angiofibroma.

Particularly in the case of cancer, vaccination with the immunogens proposed by the present invention results effective in the treatment of carcinomas, sarcomas and vascularized tumors. Some examples of tumors that can be treated with the proposed strategies include epidermoid tumors, squamous tumors like those of the head and neck, and colorectal, prostate, breast, lung (including small and non-small cells), pancreas, thyroid, ovary, and liver tumors. These methods are also effective in the treatment of other types of tumors, like Kaposi sarcoma, central nervous system neoplasia (neuroblastoma, capillary hemangioma, meningioma and brain metastasis), melanomas, renal and gastrointestinal carcinomas, rhabdomyosarcoma, glioblastoma and leiomiosarcoma.

Specifically the use of VEGF-A and/or their receptors VEGFR-1 and VEGFR-2 as immunogen is useful for the treatment of: tumors of different origins and localizations and their metastasis, of hemangioma, of endometriosis, of tissue edemas, of chronic inflammatory processes like ulcerative colitis and Crohn's disease, of, atherosclerosis, of rheumatoid arthritis and osteoarthritis, of inflammatory arthropathies, psoriasis, respiratory distress, asthma, thyroiditis, of diabetic and newborn retinopathies, macular degeneration, and glaucoma, of the autosomic VHL disease, of obesity, and of the rejection of some organ transplants. On the other hand, a response vs PlGF is useful in cases of rheumatoid arthritis and in general for the treatment of primary inflammatory arthropathies.

In the case of VEGF-B, its use as immunogen results useful in cases of breast, ovary, and kidney tumors, and for melanoma and fibrosarcoma. The use of VEGF-C and its receptor VEGFR-3 results useful in the treatment of tissular edema, diabetic retinopathy, chronic inflammation, ulcers, and tumors of the breast, lung, head and neck, esophagus, stomach, lymphomas, and prostate, metastatic nodules and Kaposi sarcoma, Dabska type hemangioendothelioma and of the cutaneous lymphangiomatosis. Immunization with VEGF-D can be used specifically for the treatment of lymphatic node metastasis.

The use of NRP1 and NRP2 co-receptors in mammal immunization results useful for the treatment, in particular, of fibrovascular proliferation in prostate cancer, melanoma, osteosarcoma, breast cancer metastasis, diabetic retinopathy, and rheumatoid arthritis.

The studies based on the passive immunotherapy by administration of antibodies have shown that the combination of antibodies vs VEGF-A and KDR is more effective in models of syngeneic tumors. Thus, the use of two or more of the immunogens proposed in the present invention provides an especially efficient treatment for the inhibition of angiogenesis and tumor growth. These immunogens can be administered in an individual manner or by pairs using bi-cistronic vectors by the already mentioned pathways. Furthermore, vaccine compositions of the invention can be used together with, or in sequential manner, with drugs or chemotherapeutic agents, that offer a benefit to the condition under treatment.

The results described below demonstrate that the anti-angiogenic and anti-tumor responses are mediated by a cooperation of the humoral and cellular responses. In particular, VEGF and its receptor are involved in the process of maturation of dendritic cells and act on B and T lymphocytes precursors. Example 10 demonstrates that the proposed therapeutic strategy, apart from diminishing the levels of VEGF in sera also contributes to the normalization of the proportions of B and T lymphocytes, and of mature dendritic cells. This effect favors the presentation of tumor antigens within the MHC I context, improving the quality and intensity of the immune anti-tumor response directed not only to the immunogen, but also to the other tumor-associated, tumor-specific, and over-expressed antigens, in the tumor context.

TABLE 1

Estimation of the VEGF protein family MHCI associated peptides in the context of HLA A.0201

A. - Using BIMAS software

| | VEGF-A | | | VEGF-B | | | VEGF-C | |
|---|---|---|---|---|---|---|---|---|
| SEQ ID | Secuencia | Kd | SEQ ID | Secuencia | Kd | SEQ ID | Secuencia | Kd |
| 27 | LLSWVHWSL | 272 | 37 | LLLAALLQL | 309 | 47 | YLSKTLFEI | 640 |
| 28 | ALLLYLHHA | 42 | 38 | QLAPAQAPV | 70 | 48 | TLFEITVPL | 324 |
| 29 | WSLALLLYL | 30 | 39 | QLVPSCVTV | 70 | 49 | VLYPEYWKM | 304 |
| 30 | FLQHNKCEC | 23 | 40 | LMGTVAKQL | 26 | 50 | CMNTSTSYL | 85 |
| 31 | WVHWSLALL | 20 | 41 | LLAALLQLA | 19 | 51 | KLFPSQCGA | 64 |
| 32 | FLLSWVHWS | 16 | 42 | LLQLAPAQA | 8 | 52 | LLGFFSVAC | 32 |
| 33 | RQLELNERT | 6 | 43 | VVSWIDVYT | 6 | 53 | SLPATLPQC | 11 |
| 34 | NITMQIMRI | 3 | 44 | CVPTGQHQV | 6 | 54 | GLQCMNTST | 7 |

TABLE 1-continued

Estimation of the VEGF protein family MHCI associated peptides in the context of HLAA.0201

| SEQ ID | Secuencia | Kd | SEQ ID | Secuencia | Kd | SEQ ID | Secuencia | Kd |
|---|---|---|---|---|---|---|---|---|
| 35 | YCHPIETLV | 2 | 45 | KQLVPSCVT | 4 | 55 | AAFESGLDL | 4 |
| 36 | IEYIFKPSC | 2 | 46 | VVVPLTVEL | 3 | 56 | EQLRSVSSV | 4 |

| VEGF-D | | | PIGF | | |
|---|---|---|---|---|---|
| SEQ ID | Secuencia | Kd | SEQ ID | Secuencia | Kd |
| 57 | FMMLYVQLV | 1966 | 67 | RLFPCFLQL | 150 |
| 58 | KLWRCRLRL | 620 | 68 | VVSEYPSEV | 42 |
| 59 | QLFEISVPL | 324 | 69 | VMRLFPCFL | 42 |
| 60 | YISKQLFEI | 88 | 70 | RALERLVDV | 34 |
| 61 | CMNTSTSYI | 41 | 71 | VELTFSQHV | 32 |
| 62 | VLQEENPLA | 35 | 72 | AVPPQQWAL | 14 |
| 63 | WVVVNVFMM | 27 | 73 | LQLLAGLAL | 14 |
| 64 | VNVFMMLYV | 10 | 74 | RSGDRPSYV | 10 |
| 65 | SLICMNTST | 7 | 75 | LLAGLALPA | 8 |
| 66 | CVLQEENPL | 7 | 76 | CVPVETANV | 6 |

B. - Using SYFPEITHI software

| VEGF-A | | | VEGF-B | | | VEGF-C | | |
|---|---|---|---|---|---|---|---|---|
| SEQ ID | Secuencia | Score | SEQ ID | Secuencia | Score | SEQ ID | Secuencia | Score |
| 77 | LLSWVHWSL | 24 | 87 | LLLAALLQL | 29 | 97 | TLFEITVPL | 27 |
| 78 | ALLLYLHHA | 24 | 88 | QLAPAQAPV | 26 | 98 | DLEEQLRSV | 26 |
| 79 | WVHWSLALL | 20 | 89 | QLVPSCVTV | 26 | 99 | YLSKTLFEI | 26 |
| 80 | SLALLLYLH | 20 | 90 | VVVPLTVEL | 24 | 100 | ALLPGPREA | 24 |
| 81 | SYCHPIETL | 19 | 91 | LLRRLLLAA | 23 | 101 | CMNTSTSYL | 21 |
| 82 | NITMQIMRI | 19 | 92 | LLAALLQLA | 23 | 102 | DICGPNKEL | 21 |
| 83 | FLLSWVHWS | 18 | 93 | FLRCQGRGL | 22 | 103 | AAAAFESGL | 20 |
| 84 | WSLALLLYL | 18 | 94 | LTVELMGTV | 21 | 104 | AAFESGLDL | 20 |
| 85 | HPIETLVDI | 18 | 95 | LRRLLLAAL | 20 | 105 | VLYPEYWKM | 20 |
| 86 | CNDEGLECV | 18 | 96 | LMGTVAKQL | 19 | 106 | IIRRSLPAT | 20 |

| VEGF-D | | | PIGF | | |
|---|---|---|---|---|---|
| SEQ ID | Secuencia | Score | SEQ ID | Secuencia | Score |
| 107 | FMMLYVQLV | 25 | 117 | ALERLVDVV | 26 |
| 108 | QLFEISVPL | 25 | 118 | RLFPCFLQL | 24 |
| 109 | YISKQLFEI | 24 | 119 | RALERLVDV | 24 |
| 110 | KLWRCRLRL | 23 | 120 | LLAGLALPA | 22 |
| 111 | RAASSLEEL | 22 | 121 | LAGLALPAV | 22 |
| 112 | SLEELLRIT | 22 | 122 | VMRLFPCFL | 20 |
| 113 | ATFYDIETL | 22 | 123 | CFLQLLAGL | 20 |
| 114 | EISVPLTSV | 22 | 124 | QLLAGLALP | 20 |
| 115 | SLICMNTST | 20 | 125 | SAGNGSSEV | 20 |
| 116 | VPLTSVPEL | 20 | 126 | VVSEYPSEV | 20 |

Note: Values in bold correspond to those peptides or their regions, which coincide in both predictions.

TABLE 2

Estimation of VEGF family receptors MHCI associated peptides in the context of HLAA.0201

A. - Using BIMAS software

| VEGFR-1 | | | VEGFR-2 | | | VEGFR-3 | | |
|---|---|---|---|---|---|---|---|---|
| SEQ ID | Secuencia | Kd | SEQ ID | Secuencia | Kd | SEQ ID | Secuencia | Kd |
| 127 | FLYRDVTWI | 1942 | 137 | VLLWEIFSL | 1792 | 147 | VLLWEIFSL | 1793 |
| 128 | VLLWEIFSL | 1792 | 138 | SLQDQGDYV | 769 | 148 | RLLEEKSGV | 1055 |
| 129 | KLLRGHTLV | 901 | 139 | VLLAVALWL | 739 | 149 | VLWPDGQEV | 981 |
| 130 | GLLTCEATV | 257 | 140 | AMFFWLLLV | 427 | 150 | NLTDLLVNV | 656 |
| 131 | TLFWLLLTL | 182 | 141 | VIAMFFWLL | 270 | 151 | KQAERGKWV | 557 |
| 132 | ILLSENNVV | 179 | 142 | ILLSEKNVV | 179 | 152 | GVIAVFFWV | 369 |
| 133 | TLNLTIMNV | 160 | 143 | LLAVALWLC | 146 | 153 | KLVIQNANV | 243 |
| 134 | CVAATLFWL | 137 | 144 | KNLDTLWKL | 128 | 154 | ALWNSAAGL | 177 |
| 135 | LLSIKQSNV | 118 | 145 | AVIAMFFWL | 113 | 155 | TLSLSIPRV | 160 |

TABLE 2-continued

Estimation of VEGF family receptors MHCI associated peptides in the context of HLA.A.0201

| 136 | SLQDSGTYA | 112 | 146 | LLLVIILRT | 108 | 156 | SQHDLGSYV | 159 |

| NRP-1 | | | NRP-2 | | |
|---|---|---|---|---|---|
| SEQ ID | Secuencia | Kd | SEQ ID | Secuencia | Kd |
| 157 | GLLRFVTAV | 2249 | 167 | WMYDHAKWL | 5121 |
| 158 | VLLGAVCGV | 1006 | 168 | ILQFLIFDL | 484 |
| 159 | WMPENIRLV | 436 | 169 | YLQVDLRFL | 247 |
| 160 | GILSMVFYT | 278 | 170 | ALYFSRHQV | 223 |
| 161 | LLCAVLALV | 272 | 171 | NMLGMLSGL | 131 |
| 162 | VLLHKSLKL | 134 | 172 | WLYTLDPIL | 129 |
| 163 | GMLGMVSGL | 131 | 173 | DIWDGIPHV | 56 |
| 164 | FQLTGGTTV | 120 | 174 | KMEIILQFL | 44 |
| 165 | VLATEKPTV | 118 | 175 | VLNKLHAPL | 36 |
| 166 | GPFLFIKFV | 81 | 176 | LLGATCAGL | 36 |

B. - Using SYFPEITHI software

| VEGFR-1 | | | VEGFR-2 | | | VEGFR-3 | | |
|---|---|---|---|---|---|---|---|---|
| SEQ ID | Secuencia | Score | SEQ ID | Secuencia | Score | SEQ ID | Secuencia | Score |
| 177 | TLFWLLLTL | 29 | 187 | VLLWEIFSL | 29 | 197 | VLLWEIFSL | 29 |
| 178 | VLLWEIFSL | 29 | 188 | LLVIILRTV | 28 | 198 | SIPGLNVTL | 27 |
| 179 | ILGPGSSTL | 28 | 189 | GLFCKTLTI | 26 | 199 | NLTDLLVNV | 27 |
| 180 | LLCALLSCL | 27 | 190 | SIMYIVVVV | 26 | 200 | VLWPDGQEV | 26 |
| 181 | GLLTCEATV | 27 | 191 | IILVGTAVI | 26 | 201 | LLPRKSLEL | 26 |
| 182 | LLRGHTLVL | 27 | 192 | ALMSELKIL | 26 | 202 | ALWNSAAGL | 26 |
| 183 | ALMTELKIL | 26 | 193 | AASVGLPSV | 25 | 203 | IMDPGEVPL | 26 |
| 184 | KLLRGHTLV | 25 | 194 | SISNLNVSL | 25 | 204 | RLWLCLGLL | 25 |
| 185 | TLNLTIMNV | 25 | 195 | AMFFQLLLV | 25 | 205 | LIYFYVTTI | 25 |
| 186 | ILLSENNVV | 25 | 196 | ILLSEKNVV | 25 | 206 | LLEGQPVLL | 25 |

| NRP-1 | | | NRP-2 | | |
|---|---|---|---|---|---|
| SEQ ID | Secuencia | Score | SEQ ID | Secuencia | Score |
| 207 | VLLGAVCGV | 30 | 217 | NMLGMLSGL | 27 |
| 208 | GLLRFVTAV | 29 | 218 | ILQFLIFDL | 26 |
| 209 | LLCAVLALV | 28 | 219 | DIWDGIPHV | 26 |
| 210 | GMLGMVSGL | 28 | 220 | YLQVDLRFL | 26 |
| 211 | ALGVLLGAV | 28 | 221 | TLDPILITI | 26 |
| 212 | VLLHKSLKL | 27 | 222 | ILAKPKMEI | 25 |
| 213 | VLATEKPTV | 26 | 223 | VLNKLHAPL | 25 |
| 214 | QLTGGTTVL | 25 | 224 | LLGATCAGL | 25 |
| 215 | VLLGAVCGV | 30 | 225 | ALYFSRHQV | 23 |
| 216 | GLLRFVTAV | 29 | 226 | GIGMRLEVL | 23 |

Note: Values in bold correspond to those peptides or their regions, which coincide in both predictions.

EXAMPLES

Example 1

Cloning and Transient Expression of Antigens.

Human VEGF, Its Isoforms and Functional Mutants

VEGF isoforms were cloned applying the polymerase chain reaction (PCR) using as template a cDNA obtained from a previous isolation of mRNA of CaSki cell line (ATCC CRL 1550), according to the manufacturer instructions (Perkin-Elmer), and utilizing primers SEQ ID NO: 1 and SEQ ID NO: 2. Bands corresponding to the amplificationproducts of VEGF isoforms 121,(SEQ ID NO: 19 and SEQ ID NO: 20), 165 and 189 were extracted from 2% agarose gels.After band digestion with endonucleases BamHI and EcoRI, the cDNAs from the VEGF isoforms were purified and cloned independently in the PAECΔ2 vector (proprietary vector of CIGB). Resulting plasmids were sequenced and determined to have no mutations with respect to the amino acid sequences reported by the EMBL for the cloned isoforms. The cDNA corresponding to VEGF isoforms were subsequently cloned KpnI/EcoRV on the pMAE5Δ5 vector that among other characteristics differs from pAECΔ2 by the presence of 5 immunostimulatory CpG sites.

cDNA from a VEGF variant deficient for the binding to the KDR receptor ($VEGF_{KDR(-)}$) was obtained by direct mutagenesis of the $VEGF_{121}$ isoform previously cloned, as described by Siemeister G et al (Siemeister G et al. J Biol Chem 273:11115, 1998).

The mutated variant SEQ ID NO: 21 and SEQ ID NO: 22 was generated by PCR using the following primers:
(A) Amplification of the 5' terminal fragment (315 bp): using primers with sequences SEQ ID NO: 3 and SEQ ID NO: 4
(B) Amplification of the 3' terminal fragment (93 bp): using primers with sequences SEQ ID NO: 5 and SEQ ID NO: 6.

The fragments thus amplified were purified as referred, and were used in equimolar concentrations as a template for a fusion PCR using the primers corresponding to sequences SEQ ID NO: 7. and SEQ ID NO: 8. Resultant cDNA containing the mutation was digested BamHI/EcoRI, and was purified, and cloned in pAECΔ2 vector. The mutations introduced were checked by sequencing, and the DNA corresponding to VEGF$_{KDR(-)}$ was subcloned KpnI/EcoRV in pMAE5Δ5 vector resulting in pMAE5Δ5 VEGF$_{KDR(-)}$.

Plasmids used both in transfection and in animal vaccination were purified in endotoxin-free conditions, as described by Whalen R. et al. (Whalen R G y Davis H L. Clin Immunol Immunopathol 75:1, 1995). Briefly, DNA was purified using QIAGEN Endo-free systems following the manufacturer instructions, and the DNA was furthermore submitted to a second precipitation. Finally, DNA was dissolved in endotoxin-free PBS (SIGMA, USA) to a final concentration of 4 mg/mL.

1.2 Human VEGF Receptor (KDR/Flk1)

The cDNAs coding for the extracellular domain of KDR receptor of VEGF (KDR1-3) and for the transmembrane and intracellular domains of this receptor (KDR TC), were obtained from an RT-PCR using mRNA of the endothelial cell line HUVEC (Clonetic, USA), treated with human VEGF (Sigma) and Heparin (Sigma).

In the case of the extracellular domains 1 to 3 SEQ ID NO: 23 and SEQ ID NO: 24the primers used correspond to sequences SEQ ID NO: 9 and SEQ ID NO: 10. After digestion of the amplified fragment (943bp) with endonucleases BamHI and EcoRI, the cDNA coding for 1-3 domains of KDR was purified, and cloned in pAECΔ2 vector. Clones positive by restriction analysis were verified by sequencing of the corresponding DNA. The cDNA corresponding to KDR 1-3 was then subcloned KpnI/EcoRV in the already described pMAE5Δ5 vector (pMAE5Δ5 KDR1-3).

For the cloning of transmembrane and cytosolic regions of the receptor (SEQ ID NO: 25 and SEQ ID NO: 26) a two-step strategy was designed. For the insertion of the first segment, the primers corresponding to SEQ ID NO: 11 and SEQ ID NO: 12 were used. After the XbaI/BglII digestion of this 747 bp segment, the product was cloned in the pMAE5 vector, previously digested with the same enzymes, obtaining the plasmid PMAE5 KDR 747. This plasmid was digested BglII/NotI in order to insert the remaining carboxi-terminal fragment of 1091 bp that was amplified using the primers corresponding to sequences SEQ ID NO: 13 and SEQ ID NO: 14. Clones positive by restriction analysis were verified by DNA sequencing and denominated pMAE5 KDR C.

1.2.1 Cloning of the Transmembrane and Cytosolic Regions of KDR in a Viral Vector For the cloning of transmembrane and cytosolic regions of VEGF receptor (KDR) on the chickenpox virus, the primers corresponding to sequences SEQ ID15 and SEQ ID16 were used. After digesting this 953 bp segment with StuI/SmaI enzymes, the product was cloned in the pFP67xgpt vector, previously digested with the same enzymes. In this same vector, digested SmaI/BamHI, the remaining 919 bp were inserted, that were amplified from the original cDNA using primers corresponding to sequences SEQ ID17 and SEQ ID18. Clones positive by restriction analysis were verified by DNA sequencing and denominated pFP67xgpt KDR C.

Chickenpox virus (FWPVs) were replicated in chicken embryo fibroblasts (CEF), in DMEM medium supplemented with 2% of fetal bovine serum (FBS). The pFP67xgpt KDR C was transfected using Lipofectin (Gibco BRL, Grand Island, USA) in CEF previously infected with the attenuated strain FP9. After 24 hours, fresh medium was added and cells were cultured for other 3 to 4 days. After this time, cells were frozen-thawed three times. Recombinant viruses expressing the gene coding for the Ecogpt enzyme were purified in selective media with mycophenolic acid (25 μg/mL), xantine (250 μg/mL), and hypoxantine (15 μg/mL) (MXH). The correct inclusion of the gene in recombinant viruses was checked by PCR. Recombinant viruses were denominated FPKDRgpt and non-recombinants used as negative control FP.

Example 2

In Vivo Expression of Antigens.

In order to confirm the potential of the constructions made to express the proteins in vivo, these were injected in the femoral quadriceps muscle of C57BL6 mice (3 per group)

1. pMAE5Δ5-$VEGF_{121}$, (10 and 50 μg/mouse) in PBS pH 7.2
2. pMAE5Δ5-$VEGF_{165}$ (10 and 50 μg/mouse) in PBS pH 7.2
3. pMAE5Δ5-$VEGF_{189}$ (10 and 50 μg/mouse) in PBS pH 7.2
4. pMAE5Δ5-$VEGF_{KDR(-)}$ (10 and 50 μg/mouse) in PBS pH 7.2
5. pMAE5Δ5-KDR 1-3 (10 and 50 μg/mouse) in PBS pH 7.2
6. pMAE5 KDR C (10 and 50 μg/mouse) in PBS pH 7.2
7. FPKDRgpt ($2.5*10^7$ cfu) in PBS pH 7.2
8. PBS pH 7.2 (negative control)

48 hours after injection the animals were sacrificed and injected muscles extracted in one piece. A part of the muscular tissue was homogenized in presence of protease inhibitors and non-ionic detergents. Presence of VEGF in protein extracts was analyzed by Dot-Blot and by Western-Blot using a polyclonal antibody that recognizes all human VEGF isoforms (sc-152G), following described procedures. RNA was extracted from the remaining muscular tissue using TR1-Reagent (SIGMA). A total of 20 μg of RNA from each experimental situation were submitted to electrophoresis in 1% agarose gels containing formaldehyde. RNA was transferred to a nylon filter (HYBOND) and hybridized with the cDNA of VEGF 121 isoform labeled with $ATP^{32}$, that recognizes all VEGF isoforms, or with the cDNA of KDR similarly labeled. In both cases, filters were re-hybridized with the cDNA corresponding to a constitutive gene: the gliceraldehyde 3-phosphate deshydrogenase (GAPDH). In all the analyzed constructions bands corresponding to human VEGF and the cloned fragments of the KDR receptor were identified.

Example 3

In Vivo Protection Experiments Employing Vaccination with the Plasmid Containing the Gene Fragments of KDR, the VEGF Receptor.

Groups of 10 C57BL/6 mice were vaccinated or not with the following variants:

1. pMAE5Δ5-KDR 1-3 (1, 10, 50 and 100 μg/mouse) in PBS pH 7.2
2. pMAE5 KDR C (1, 10, 50 and 100 μg/mouse) in PBS pH 7.2
3. FPKDRgpt ($2.5*10^7$ cfu)
4. PBS pH 7.2 (negative control)
5. FP ($2.5*10^7$ cfu) (negative control group 3)

In every case, mice were immunized by intramuscular injection (im.) in the rear left foot with a total volume of 50 μl. All the animals were re-immunized 15 days later using the original immunization regime. The tumor challenge was developed thirty days after the last immunization, by a subcutaneous (sc.) injection of $10^4$ cells of B16-F10 melanoma (ATCC, CRL-6475) in the right ventral zone of every animal. Tumor growth was monitored with three weekly measurements until animals started to die.

In mice immunized with the pMAE5Δ5-KDR 1-3 plasmid a reduction of tumor size was evidenced at doses of 50 and 100 μg of DNA/mouse, significantly lower with respect to the negative control (Table 3). A survival analysis at day 33 revealed a significant increment (with respect to the negative control) of this parameter for the animals immunized with the said DNA doses of 50 and 100 μg per mouse, with respect to the un-immunized mice (group PBS pH7.2). In the case of pMAE5Δ5-KDR C (Table 3) a significant reduction of tumor volume was observed at the four doses used, with an increment in survival for doses from 100 to 10 μg/animal. The use of viral vectors reduced the volume and increased survival in the condition used for the FPKDRgpt construction (Table 3), in comparison to the respective negative control (group of mice immunized with the vector without insert FPgpt).

TABLE 3

Tumor volume and survival in mice immunized with the fragments of the VEGF receptor (KDR) gene.

| Group | [DNA μg] | Tumor Vol. (mm$^3$) Day 24 | | Survival (Day 43) |
|---|---|---|---|---|
| pMAE5Δ5-KDR 1-3 | 100 | 424.0 ± 199.2 | (*) | (*) |
|  | 50 | 756.32 ± 435.9 | (*) | () |
|  | 10 | 1024.2 ± 397.1 | (*) | (ns) |
|  | 1 | 1334.2 ± 620.7 | (ns) | (ns) |
| pMAE5Δ5-KDR C | 100 | 404.23 ± 200.0 | (*) | (*) |
|  | 50 | 633.2 ± 365.2 | (*) | (*) |
|  | 10 | 924.3 ± 437.1 | (**) | (*) |
|  | 1 | 1114.2 ± 665.7 | (*) | (ns) |
| FPKDRgpt | 2.5 * 10$^7$ cfu | 304.23 ± 152.0 | (*) | (*) |
| FPgpt | 2.5 * 10$^7$ cfu | 1891.0 ± 726.0 | (ns) | (ns) |
| PBS pH 7.2 | — | 1785.0 ± 826.0 | | — |

Note
Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day. Statistical signification is indicated as ns, ps ≦ 0.05 non-significant; *, p ≦ 0.05; , p ≦ 0.01; and *, p ≦ 0.001.

Example 4

In Vivo Protection Experiments Using Vaccination with the Plasmids Containing the VEGF Isoforms, and the Mutated Variant.

Groups of 10 mice C57BU6 were vaccinated or not with the following variants:
1. pAECΔ2-VEGF$_{121}$ (1, 10, 50 and 100 μg/mouse) in PBS pH 7.2
2. pMAE5Δ5-VEGF$_{121}$ (1, 10, 50 and 100 μg/mouse) in PBS pH 7.2
3. pMAE5Δ5-VEGF$_{165}$ (1, 10, 50 and 100 μg/mouse) in PBS pH 7.2
4. pMAE5Δ5-VEGF$_{189}$ (1, 10, 50 and 100 μg/mouse) in PBS pH 1.2
5. pMAE5Δ5 VEGF$_{KDR(-)}$ (1, 10, 50 and 100 μg/mouse) in PBS pH 7.2
6. PBS pH 7.2 (negative control)

In every case, mice were immunized by im. injection in the rear left foot with a total volume of 50 μl. All the animals were re-immunized 15 days later using the original immunization regime. The tumor challenge was developed thirty days after the last immunization, by a subcutaneous injection of 10$^4$ cells of B16-F10 melanoma (ATCC, CRL-6475) in the right ventral zone of every animal. Tumor growth was monitored with three weekly measurements until animals started to die.

For the naked DNA variant in pAEC series in the case of mice immunized with 100 μg/animal, a decrease in tumor growth with respect to the negative control was observed (Table 4). In the variants included in the vector of the pMAE5Δ5 series with 5 CpG sites, independently of the VEGF isoform, tumor size was significantly reduced as compared to the negative control in the groups of mice immunized with doses of 10, 50, or 100 μg of DNA. In the case where the mutated variant pMAE5Δ5 VEGF$_{KDR(-)}$ was used, a significant reduction of tumor size was obtained at similar doses as those employed with the pMAE5Δ5-VEGF$_{121}$.

A survival analysis on day 43 evidenced a significant increase (with respect to the negative control) of the animals immunized with the variants pMAE5Δ5-VEGF$_{121}$ pMAE5Δ5-VEGF$_{165}$, pMAE5Δ5-VEGF$_{189}$ and pMAE5Δ5 VEGF$^{KDR(-)}$, at doses of 50 and 100 μg per animal (Table 4).

TABLE 4

Tumor volume and survival in mice immunized with different variants of naked DNA containing the different isoforms of the VEGF gene and a mutated variant.

| Group | [DNA μg] | Tumor Vol. (mm$^3$) (Day 24) | | Survival (Day 43) |
|---|---|---|---|---|
| PAECΔ2-VEGF$_{121}$ | 100 | 991.5 ± 354 | (*) | ns |
|  | 50 | 1429.2 ± 396 | (ns) | ns |
|  | 10 | 1506.6 ± 442 | (ns) | ns |
|  | 1 | 1660.5 ± 456 | (ns) | ns |
| PMAE5Δ5-VEGF$_{121}$ | 100 | 645.0 ± 215 | (***) | *** |
|  | 50 | 850.1 ± 463 | (***) | *** |
|  | 10 | 992.1 ± 410 | (*) | ns |
|  | 1 | 1560.3 ± 598 | (ns) | ns |
| PMAE5Δ5-VEGF$_{165}$ | 100 | 799.2 ± 335 | (***) | *** |
|  | 50 | 916.6 ± 390 | (**) | ** |
|  | 10 | 1000.5 ± 662 | (*) | ns |
|  | 1 | 1845.3 ± 450 | (ns) | ns |
| PMAE5Δ5-VEGF$_{189}$ | 100 | 790.1 ± 235 | (***) | *** |
|  | 50 | 996.5 ± 255 | (*) | ** |
|  | 10 | 1050.2 ± 362 | (*) | ns |
|  | 1 | 1670.2 ± 408 | (ns) | ns |
| pMAE5Δ5 VEGF$_{KDR(-)}$ | 100 | 550.1 ± 335 | (***) | *** |
|  | 50 | 894.7 ± 408 | (**) | *** |
|  | 10 | 991.8 ± 362 | (*) | ns |
|  | 1 | 1489.3 ± 510 | (ns) | ns |
| PBS pH 7.2 | 0 | 1673.9 ± 712 | | |

Note:
Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day. Statistical signification is indicated as ns, p ≦ 0.05 non-significant; *, p ≦ 0.05; , p ≦ 0.01; and *, p ≦ 0.001.

Example 5

In Vivo Protection Experiments through Immunization with pMAE5Δ5-VEGF$_{121}$ and pMAE5Δ5-KDR 1-3, in a Model of Collagen-Induced Arthritis, Groups of 20 mice were vaccinated or not with the following variants:
1. pMAE5Δ5-VEGF$_{121}$ (50 μg of DNA/mouse) in PBS pH 7.2
2. pMAE5Δ5-KDR 1-3 (50 μg of DNA/mouse) in PBS pH 7.2
3. PBS pH 7.2 (Negative control)

In all cases immunization (day 0) was by im. route in the rear left foot with a total volume of 50 μl. All the animals were re-immunized 15 days later using the original immunization regime.

On day 5 the induction of autoimmune arthritis began by immunization with chicken collagen type II (Sigma), a model previously described by Campbell et al. (Campbell I K et al Eur. J. Immunol. 30: 1568, 2000). This immunization was repeated on day 26. The four extremities of each mouse were evaluated on a daily basis according to the arthritis index that establishes punctuation from 0 to 3 for each limb due to the presence in the examination of signs of erythema (1), inflammation (2), or articular rigidity (3), with a maximal value of 12. Mice started to show clinical symptoms of arthritis development 23 days after the induction, with the higher incidences at 50 days. Table 5 shows the analysis of arthritis incidence in the animals of the different experimental groups. In days 40 and 55 a significant reduction on arthritis incidence was observed in vaccinated groups (1 and 2) as compared to control group.

TABLE 5

Incidence of arthritis on selected days (40 and 55).

| Group | Incidence day 40 | Incidence day 55 |
|---|---|---|
| 1 | 20/8 (40%) | 20/9 (45%) |
| 2 | 20/6 (30%) | 20/12 (60%) |
| 3 | 20/10 (50%) | 20/14 (70%) |

Example 6

In Vivo Antiangiogenic Effect of Vaccination

Groups of 15 mice were vaccinated or not with the following variants:
1. pMAE5Δ5-VEGF$_{121}$ (50 μg of DNA/mouse) in PBS pH 7.2
2. pMAE5Δ5-KDR 1-3 (50 μg of DNA/mouse) in PBS pH 7.2
3. pMAE5 KDR C (50 μg/mouse) in PBS pH 7.2
4. PBS pH 7.2 (Negative control)

In every case, C57BI/6 mice were immunized by im. injection in the rear left foot with a total volume of 50 μl. All the animals were re-immunized 15 days later using the original immunization regime. Thirty days after the last immunization, the in vivo angiogenesis was evaluated in the animals using matrigel as described by Coughlin M C et al. (Coughlin M C et al. J. Clin. Invest. 101:1441, 1998). The animals previously vaccinated were divided in groups of 5 and injected subcutaneously in the abdominal middle line with 500 μl of matrigel (Becton Dickinson and Co., Franklin Lakes, N.J., USA) containing:
1. VEGF 50 ng/mL, Heparin 50 U/mL
2. $10^5$ cells of B16-F10 melanoma
3. PBS Six days later the animals were sacrificed and the matrigel plug was extracted. Hemoglobin contents in the plugs were analyzed according to the manufacturer instructions (Drabkin's reagent kit; Sigma Diagnostics Co., St. Louis, Mo., USA). Vaccination with the plasmids coding for VEGF or its receptor KDR inhibit significantly (p<0.001) the VEGF induced vascularization, as well as that induced by systems that are more complex: tumor cells.

Example 7

Obtainment of an Immunogen Based in the Non-Covalent Binding of pMAE5Δ5-VEGF$_{121}$ to Different Adjuvant Agents.

Different immunostimulatory agents, previously reported, were used, mixed with the pMAE5Δ5-VEGF$_{121}$ construction following with the methodology described below.

The Opc protein from the outer membrane of *Neisseria meningitidis* was purified according to the report of Musacchio et al. (Musacchio A et al. Vaccine, 67:751, 1997). 50 μg/mL of pMAE5Δ5-VEGF$_{121}$ were added to 10 μg/mL of Opc with gentle shaking at acid pH. The resulting complex was extensively dialyzed overnight in endo-free PBS pH 7.2 (Sigma). The level of Opc protein-plasmid DNA association (Opc-pMAE5Δ5-VEGF$_{121}$) was checked by DNA visualization using 1% agarose gel. More than 50% of the plasmid DNA was associated to the Opc protein.

Very small particles (VSSP) coming from complex of outer membrane proteins (OMPC) of *Neisseria meningitides*, supplied by the Center of Molecular Immunology (R. Perez et al. U.S. Pat. No. 5,788,985, and 6,149,921), were used for combination with the plasmid DNA of interest. VSSP (1 mg) were incubated with 5 mg of pMAE5Δ5-VEGF$_{121}$ overnight with gentle agitation. The resulting material was extensively dialyzed in endo-free PBS pH 7.2 (Sigma). The level of VSSP-plasmid DNA association (VSSP-pMAE5Δ5-VEGF$_{121}$) was checked by DNA visualization using 1% agarose gel. More than 50% of the plasmid DNA was associated to the VSSP particles.

The Hepatitis C and Hepatitis B core particulated antigens (HCcAg and HBcAg) were produced according to a previous report (Lorenzo L J et al., Biochem Biophys Res Commun 281:962, 2001). One mg of the antigens were mixed with 5 mg of the plasmid in an overnight incubation. The levels of HCcAg or HBcAg-plasmid DNA association (HCcAg-pMAE5Δ5-VEGF$_{121}$ and HBcAg-pMAE5Δ5-VEGF$_{121}$, respectively) were checked by DNA visualization using 1% agarose gel. More than 50% of the DNA was associated to the antigenic particle, in each case.

Example 8

Experiments of In Vivo Protection with the pMAE5Δ5-VEGF$_{121}$ construction and immune response adjuvants.

Groups of 10 C57BL/6 mice were vaccinated or not with the following variants:
1. pMAE5Δ5-VEGF$_{121}$ (1, 10 and 50 μg of DNA/mouse) in PBS pH 7.2
2. Opc-pMAE5Δ5-VEGF$_{121}$ (1, 10 and 50 μg of DNA/mouse)
3. VSSP-pMAE5Δ5-VEGF$_{121}$ (1, 10 and 50 μg of DNA/mouse)
4. HBcAg-pMAE5Δ5-VEGF$_{121}$ (1,10 and 50 μg of DNA/mouse)
5. HCcAg-pMAE5Δ5-VEGF$_{121}$ (1, 10 and 50 μg of DNA/mouse)
6. PBS pH 7.2 (Negative control for group 1)
7. Opc (Negative control for group 2)
8. VSSP (Negative control for group 3)
9. HBcAg (Negative control for group 4)
10. HCcAg (Negative control for group 5)

Immunization procedures, as well as tumor challenge and tumor volume measurements were similar to those described in the previous example. The vaccine variants with doses similar or higher to 10 μg of DNA/mouse decreased tumor growth in comparison to the respective negative controls (Table 6). A significant superior survival as compared to that of the respective control, was observed for the animals immunized with the VEGF gene, associated or not with Opc, VSSP, HCcAg and HbcAg, as immunopotentiator vehicles. All the variants with vehicle showed a significant superior survival versus the respective control, for doses starting with 10 μg/mouse, while the naked DNA variant with the vector pMAE5Δ5-VEGF$_1$2, resulted significantly different from the negative control at the dose of 50 μg/mouse (Table 6).

TABLE 6

Tumor volume and survival of mice immunized using different immunostimulatory agents.

| Group | [DNA µg] | Tumor Vol. (mm³). (Day 24) | | Survival (Day 43) |
|---|---|---|---|---|
| pMAE5Δ5-VEGF | 50 | 1050.9 ± 689 | (**) | ns |
|  | 10 | 1229.0 ± 596 | (*) | ns |
|  | 1 | 1895.3 ± 596 | (ns) | ns |
| OpC-pMAE5Δ5-VEGF | 50 | 960.6 ± 456 | (**) | ** |
|  | 10 | 1100.5 ± 615 | (**) | * |
|  | 1 | 1654.8 ± 663 | (ns) | ns |
| VSSP-pMAE5Δ5-VEGF | 50 | 884.6 ± 410 | (***) | ** |
|  | 10 | 1002.3 ± 598 | (**) | * |
|  | 1 | 1532.7 ± 745 | (ns) | ns |
| HBcAg-pMAE5Δ5-VEGF | 50 | 950.1 ± 570 | (**) | ** |
|  | 10 | 1230.5 ± 662 | (*) | * |
|  | 1 | 1867.2 ± 652 | (ns) | ns |
| HCcAg-pMAE5Δ5-VEGF | 50 | 950.1 ± 570 | (**) | ** |
|  | 10 | 1230.5 ± 662 | (*) | * |
|  | 1 | 1867.2 ± 652 | (ns) | ns |
| OpC (5 µg/mouse/dose) | 5 µg | 2059.0 ± 687 | (ns) | ns |
| VSSP |  | 2156.0 ± 759 | (ns) | ns |
| HBcAg (5 µg/mouse/dose) |  | 1998.2 ± 798 | (ns) | ns |
| HCcAg (5 µg/mouse/dose) |  | 1897.0 ± 812 | (ns) | ns |
| PBS pH 7.2 |  | 2073.0 ± 816 | (ns) | ns |

Note:
Tumor volume is reported as mean standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day. Statistical signification is indicated as ns, $p \leq 0.05$ non-significant; *, $p \leq 0.05$; , $p \leq 0.01$; and *, $p \leq 0.001$.

Example 9
In Vivo Protection Experiment Using VEGF in Its Protein Form.

Groups 10 C57BU6 mice were vaccinated or not with the following variants: VEGF165 (20 µg/mouse) with Complete and Incomplete Freund adjuvant Complete and Incomplete Freund adjuvant (negative control).

$VEGF_{165}$ antigen was obtained from a commercial source (SIGMA) with more than 97% purity. Mice were immunized by the intraperitoneal route using Complete Freund's adjuvant (Sigma) with re-immunizations in days 15 and 30 by the same route but using Incomplete Freund's adjuvant. Tumor challenge, and measurements of tumor volume were similar to those described in the previous example.

A significant reduction in tumor volume and increase survival were observed in the VEGF immunized group as compared to the control non-immunized group. The effect was similar to those found in previous experiments using VEGF DNA.

Example 10
In Vivo Experiments of Immune Protection Transfer in C57BU6 Mice with Severe Combined Immunodeficiency (SCID).

C57BL/6 mice were immunized or not with doses of 50 µg of pMAE5Δ5-$VEGF_{121}$ DNA/mouse using the procedures described in the example 5. Mice were sacrificed at 45 days after first immunization. CD8+, CD4+ and B-lymphocytes of these mice were separated using magnetic beads (Dynabeads, USA), according to the manufacturer instructions.

Groups of 10 six-week old C57BL/6 SCID mice were reconstituted with the following combinations of the previously extracted lymphocytes.

Group 1: CD8+ T-lymphocytes and CD4+ T-lymphocytes from mice immunized with pMAE5Δ5-$VEGF_{121}$ DNA. B-lymphocytes were not reconstituted.

Group 2: B-lymphocytes and CD4+ T-lymphocytes from immunized mice, and CD8+ T-lymphocytes from non-immunized mice.

Group 3: B-lymphocytes, CD8+ T-lymphocytes and CD4+ T-lymphocytes from immunized mice, as a positive control of the experiment.

Group 4: B-lymphocytes, CD8+ T-lymphocytes, and CD4+ T-lymphocytes from non-immunized mice, as a negative control of the experiment.

Reconstituted SCID mice were challenged sc. with $10^4$ B16-F10 melanoma cells. Tumor growth was monitored by three weekly measurements until mice start to die. Anti-VEGF antibody levels were analyzed through a laboratory ELISA. 96-well plates were incubated overnight with a 0.5 µg/ml solution of VEGF165 (Sigma). The wells were blocked with PBS-BSA 1% (BDH, UK) solution, and later incubated with serial dilutions of the animal sera. After washing with PBS-Tween 0.05%, a commercially available polyclonal anti mouse IgG (Sigma, A0168) was added. The signal was amplified in the presence of the commercial substrate ortho-phenilene-diamine (OPD, Sigma).

Table 7 reflects the results of tumor volume (Day 24) and survival (Day 40) of the groups of mice submitted to tumor challenge. Beginning on the day 15 after reconstitution, the animals of the groups 1 to 3 experienced a reduction in tumor size as compared to group 4, reconstituted with lymphocytes from non-immunized mice. Thus, the effect that provokes the immune system in the immunized mice, that allows the reduction in tumor size, is related to humoral and cellular responses, being the last one of the cytotoxic type (CTL), due to the absence of anti-VEGF antibodies in group 1. Nevertheless, in the experimental conditions used survival only increased in group 3 (B and T lymphocytes of immunized mice), as compared to the rest of the groups (Table 7). In the partially reconstituted animals where B or T of the CTL type responses were absent (groups 1 and 2, respectively) the survival was not different from the negative control. These results demonstrate that the combination of humoral and cellular responses (group 4), have a synergic effect that enables an effective response able to prolong the survival of mice submitted to the tumor challenge.

TABLE 7

Tumor volume and survival in SCID mice reconstituted with lymphocytes from pMAE5Δ5-$VEGF_{121}$ immunized mice.

| | Mice donating lymphocytes to the C57BL/6 SCID | | | Tumor Vol. | Survival |
|---|---|---|---|---|---|
| Group | B Lymph. | CD4+ Lymph. | CD8+ Lymph. | (Day 24) | (Day 40) |
| 1 | — | immunized | immunized | 1067.8 ± 689 (ns) | ns |

TABLE 7-continued

Tumor volume and survival in SCID mice reconstituted with lymphocytes from pMAE5Δ5-VEGF$_{121}$ immunized mice.

| | Mice donating lymphocytes to the C57BL/6 SCID | | | Tumor Vol. | Survival |
|---|---|---|---|---|---|
| Group | B Lymph. | CD4+ Lymph. | CD8+ Lymph. | (Day 24) | (Day 40) |
| 2 | immunized | immunized | non immunized | 1129.0 ± 596 (ns) | ns |
| 3 | immunized | immunized | immunized | 652.3 ± 396 (***) | *** |
| 4 | Non immunized | Non immunized | Non immunized | 1856.0 ± 756 | — |

Note:
Donor mice were immunized or not with doses of 50 μg of pMAE5Δ5-VEGF DNA per mouse. Tumor volume is reported as mean ± standard deviation (SD) of the measures performed on the animals of each group, statistical comparisons were performed using one-way ANOVA and a Bonferroni post-test. In the case of survival, the reported statistical significance was obtained using the log-rank test to compare each group with respect to the control group, in the indicated day. Statistical signification is indicated as ns, $p \leq 0.05$ non-significant; *, $p \leq 0.05$; , $p \leq 0.01$; and *, $p \leq 0.001$.

Example 11

Demonstration of Immunological Restoration by Depletion of Circulant VEGF through Immune Response.

Groups of 15 C57BU6 female mice were injected by im. route with the following variants:
1. pMAE5Δ5-VEGF$_{121}$ (50 μg/mouse) in PBS pH 7.2
2. PBS pH 7.2

In every case, mice were immunized by im. injection in the rear left foot with a total volume of 50 μl. All the animals were re-immunized 15 days later using the original immunization regime. Thirty days after the last immunization 5 randomly selected animals from each group were sacrificed to analyze the immunological state of the immunized and control animals, as well as the toxicity of vaccination on organs and tissues, through macroscopic and histological evaluations.

Remaining animals of each group received a sc injection of $10^4$ melanoma B16-F10 cells in the right ventral zone. At 15 and 30 days after tumor cells injection, 5 mice per group were sacrificed and evaluated as previously described.

Toxic events were not evidenced at macroscopic level in any of the evaluated animals, and histopathological analysis reveal no damage in any of the organs examined 30 days after the last immunization. Immunological evaluation consisted of: (1) evaluation of murine VEGF levels in serum; (2) cellular content of T and B lymphocytes, as well as the degree of maturity of dendritic cells in spleen, and in brachial axillary and inguinal lymph nodes.

The analysis of the levels of murine VEGF (R&D kit for murine VEGF) in the sera of un-treated animals showed that with the increase of time of exposure to tumor, the VEGF levels increased in serum, in concordance with the increase of tumor size with time. In the group immunized against human VEGF a significant reduction (p<0.001 ANOVA, post-test Bonferroni) of murine VEGF levels was detected, that lasted past 30 days after the tumor challenge.

The status of the immune system of the animals sacrificed on each moment was analyzed through the study of the proportions of the cellular populations present on lymph nodes and spleen, according to the reports of Gabrilovich et al. (Gabrilovich D et al. Blood 92:4150, 1998). For theses studies, commercial monoclonal antibodies that recognize CD3, CD19, CD11c and CD86 (B7-2) molecules (Pharmingen) labeled with fluorescein isothiocyanate (FITC) and phycoerythrine (PE), were used, that allowed the visualization of the cellular populations using a flow cytometer (FACS). Results obtained are shown in table 8.

TABLE 8

Summary of the results of FACS analysis of cell populations according to surface markers.

| | Total of Cells | | | | Fraction enriched with dendritic cells | |
|---|---|---|---|---|---|---|
| | Lymph Nodes | | Spleen | | Lymph Nodes | Spleen |
| Group (day) | CD-19 | CD-3 | CD-19 | CD-3 | CD-11c/B7-2 | CD-11c/B7-2 |
| A. Non immunized | | | | | | |
| Non immunized (30 Days) | 8% | 86% | 38.1% | 40.8% | 60% | 62.4% |
| After tumor challenge (60 Days) | 20.1% | 60.5% | 3.8 | 11.4% | 32.8% | 10.2% |
| B. Immunized | | | | | | |
| Immunized (30 Days) | 7.2% | 87.3% | 40% | 39% | 58.6% | 60.3% |

TABLE 8-continued

Summary of the results of FACS analysis of cell populations according to surface markers.

| | Total of Cells | | | | Fraction enriched with dendritic cells | |
|---|---|---|---|---|---|---|
| | Lymph Nodes | | Spleen | | Lymph Nodes | Spleen |
| Group (day) | CD-19 | CD-3 | CD-19 | CD-3 | CD-11c/B7-2 | CD-11c/B7-2 |
| After tumor challenge (60 Days) | 10.9% | 80.1% | 25.4 | 34% | 53.5% | 52.9% |

Note:
In every case, values indicate the percent of positive cells from the total of quantified cells.

The analyses of lymphoid cell populations and of the maturation of dendritic cells in the animals, 30 days after the immunization, indicate that the vaccination with the VEGF DNA does not induce any change in the immune status of the animal. Nevertheless, 30 days after the tumor implantation, the non-vaccinated animals show a decrease in the T-lymphocyte/B-lymphocyte ratio (CD3/CD19) both in lymph nodes and in spleen, with respect to the ratio before the tumor challenge. Furthermore, in particular in the spleen, there is a significant reduction in the number of lymphoid cells. A reduction in the number of mature dendritic cells both in lymph nodes and in spleen was also observed in these animals. In the group of mice vaccinated with the VEGF DNA a significant recovery in all parameters was evidenced, that could be correlated with the reduction of the VEGF levels in the sera observed in the animals of this group.

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on Oct. 31, 2008. The sequence_listing.txt file is 58kb in size.

The invention claimed is:

1. An immunogenic composition comprising an autologous VEGF-A polypeptide impaired for receptor activation identified as the amino acid sequence set forth in SEQ ID NO: 21 or fragments thereof identified as the amino acid sequence set forth in SEQ ID NO: 27 to SEQ ID NO: 36 and SEQ ID NO: 77 to SEQ ID NO: 86; and at least one of the molecules described in:

a) VEGFR2 polypeptide fragments identified as the amino acid sequence set forth in SEQ ID NO: 137 to SEQ ID NO: 146 and SEQ ID NO: 187 to SEQ ID NO: 196;

b) VEGFR2 polypeptide fragments identified as the amino acid sequence set forth in SEQ ID NO: 137 to SEQ ID NO: 146 and SEQ ID NO: 187 to SEQ ID NO: 196, said composition being mixed with or fused to p64K protein of *Neisseria meningitides*;

c) VEGFR2 polypeptide fragments identified as the amino acid sequence set forth in SEQ ID NO: 137 to SEQ ID NO: 146 and SEQ ID NO: 187 to SEQ ID NO: 196, said composition being mixed with or noncovalently bound to very small particles (VSSP) from complex of outer membrane proteins of *Neisseria meningitides*;

d) VEGFR2 polypeptide fragment identified as the amino acid sequence set forth in SEQ ID NO: 23;

e) VEGFR2 polypeptide fragment identified as the amino acid sequence set forth in SEQ ID NO: 23, said composition being mixed with or fused to p64K protein of *Neisseria meningitides*;

f) VEGFR2 polypeptide fragment identified as the amino acid sequence set forth in SEQ ID NO: 23, said composition being mixed with or from complex of outer membrane proteins of *Neisseria meningitides*;

g) VEGFR2 polypeptide fragment identified as VEGF-A SEQ ID NO: 25;

h) VEGFR2 polypeptide fragment identified as VEGF-A SEQ ID NO: 25, said composition being mixed with or fused to p64K protein of *Neisseria meningitides*; or i) VEGFR2 polypeptide fragment identified as VEGF-A SEQ ID NO: 25, said composition being mixed with or noncovalently bound to very small particles (VSSP) from comples of outer membrane proteins of *Neisseria meningitides*;

and optionally further comprising a pharmaceutically accepted adjuvant.

2. The immunogenic composition according to claim 1, wherein the adjuvant is selected from the group consisting of recombinant particle of Hepatitis B Core Antigen, recombinant particle of Hepatitis C Core Antigen, OPC protein, KLH protein, *Neisseria meningitides* p64k protein, very small particles (VSSP) from complex of outer membrane proteins of *Neisseria meningitides*.

* * * * *

UNITED STATES PATENT AND TRADEMARK OFFICE
CERTIFICATE OF CORRECTION

PATENT NO. : 7,556,809 B2
APPLICATION NO. : 10/511384
DATED : July 7, 2009
INVENTOR(S) : Romero et al.

It is certified that error appears in the above-identified patent and that said Letters Patent is hereby corrected as shown below:

Column 1, line 48

Now reads: "VEGF-BNRF, VEGF-CHRP";

Should read: -- VEGF-B/VRF, VEGF-C/VRP --.

Column 3, line 67 – Column 4, line 1

Now reads: "tymphangiomatosis";

Should read: -- lymphangiomatosis --.

Column 19, lines 49-50

Now reads: "in PBS pH 1.2";

Should read: -- in PBS pH 7.2 --.

Column 22, line 66

Now reads: "pMAE5Δ5-VEGF$_1$2, resulted";

Should read: -- pMAE5Δ5-VEGF$_{121}$, resulted --.

Column 23, line 36

Now reads: "Groups 10 C57BU6 mice";

Should read: -- Groups 10 C57BL/6 mice --.

Column 23, line 54

Now reads: "C57BU6 Mice with";

Should read: -- C57BL/6 Mice with --.

UNITED STATES PATENT AND TRADEMARK OFFICE
CERTIFICATE OF CORRECTION

PATENT NO.       : 7,556,809 B2
APPLICATION NO.  : 10/511384
DATED            : July 7, 2009
INVENTOR(S)      : Romero et al.

It is certified that error appears in the above-identified patent and that said Letters Patent is hereby corrected as shown below:

Column 25, line 26

Now reads:    "Groups of 15 C57BU6 female";

Should read:    -- Groups of 15 C57BL/6 female --.

Column 34, line 35

Now reads:    "from comples of outer";

Should read:    -- from complex of outer --.

Signed and Sealed this

Sixth Day of October, 2009

David J. Kappos
*Director of the United States Patent and Trademark Office*

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
tggatccatg aactttctgc t                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 2
gaattcaccg cctcggcttg tc                                             22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
tggatccatg aactttctgc t                                              21

<210> SEQ ID NO 4
```

```
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4
ctggccttgt gcaggtgcga ttgccataat                                          30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 5
attatggcaa tcgcacctgc acaaggccag                                          30

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 6
gaattcaccg cctcggcttg tc                                                  22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 7
tggatccatg aactttctgc t                                                   21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
gaattcaccg cctcggcttg tc                                                  22

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 9
tggatccatg gagagcaagg tgctg                                               25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 10
```
gaattcacat cagcccactg gatgc                                              25

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
cctctagatg tgcaaaagtg g                                                  21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 12
tgagatcttc gggagcttcc                                                    20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 13
gaagatctgt ataaggactt c                                                  21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 14
tagcggccgc ttaaacagg                                                     19

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 15
aggcctctac acctgccagg ca                                                 22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
cctaggttaa acaggaggag                                                    20

<210> SEQ ID NO 17
<211> LENGTH: 21
<212> TYPE: DNA

-continued

```
<213> ORGANISM: Artificial Sequence
<220> FEATURE:
<223> OTHER INFORMATION: Description of Artificial Sequence: primer

<400> SEQUENCE: 17
cccgggatat ttataaagat c                                              21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 18
tagcggccgc ttaaacagg                                                 19
```